(12) United States Patent
Lee (10) Patent No.: US 12,310,784 B2
(45) Date of Patent: May 27, 2025

(54) ULTRASONIC PROBE

(71) Applicant: SAMSUNG MEDISON CO., LTD., Gangwon-do (KR)

(72) Inventor: Jun Yeol Lee, Gangwon-do (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 46 days.

(21) Appl. No.: 17/417,664

(22) PCT Filed: Jul. 23, 2019

(86) PCT No.: PCT/KR2019/009072
§ 371 (c)(1),
(2) Date: Jun. 23, 2021

(87) PCT Pub. No.: WO2020/145467
PCT Pub. Date: Jul. 16, 2020

(65) Prior Publication Data
US 2022/0054106 A1 Feb. 24, 2022

(30) Foreign Application Priority Data
Jan. 8, 2019 (KR) .................. 10-2019-0002187

(51) Int. Cl.
*A61B 8/08* (2006.01)
*A61B 17/34* (2006.01)

(52) U.S. Cl.
CPC ........ *A61B 8/0841* (2013.01); *A61B 17/3403* (2013.01); *A61B 2017/3413* (2013.01)

(58) Field of Classification Search
CPC .............. A61B 8/0841; A61B 17/3403; A61B 2017/3413; A61B 8/4483; A61B 2017/3405; A61B 8/4444
See application file for complete search history.

(56) References Cited

U.S. PATENT DOCUMENTS 5,758,650 A * 6/1998 Miller ................ A61B 17/3403
600/461
6,296,614 B1 * 10/2001 Pruter ................ A61B 17/3403
600/461
(Continued)

FOREIGN PATENT DOCUMENTS

CN      109394315 A   *  3/2019    ......... A61B 17/3403
EP         3372177 A1       9/2018
(Continued)

OTHER PUBLICATIONS

Extended European Search Report dated Aug. 22, 2022 issued in European Patent Application No. 19909164.6.
(Continued)

*Primary Examiner* — Jason M Ip
*Assistant Examiner* — Renee C Langhals
(74) *Attorney, Agent, or Firm* — Morgan Lewis & Bockius LLP (57) ABSTRACT

The present disclosure relates to an ultrasonic probe that acquires an ultrasonic image to diagnose or treat an object using a needle.

The ultrasonic probe includes a case, a needle inserted into an object in the vicinity of the case, and a needle guide detachably mounted on the case to guide the needle, wherein the needle guide includes a base including a guide part configured such that the needle is inserted therein, and a support member configured to be movable along the guide part to support movement of the needle.

8 Claims, 9 Drawing Sheets

(56) References Cited

U.S. PATENT DOCUMENTS

| | | | |
|---|---|---|---|
| 6,361,499 | B1 | 3/2002 | Bates et al. |
| 7,691,066 | B2 * | 4/2010 | Kosaku ................ A61B 8/0833 604/117 |
| 2005/0131291 | A1 | 6/2005 | Floyd et al. |
| 2007/0167817 | A1 * | 7/2007 | Huang ................ A61B 8/0833 600/461 |
| 2008/0171940 | A1 | 7/2008 | McGahan |
| 2011/0028847 | A1 * | 2/2011 | Whitmore, III ... A61B 17/3403 600/461 |
| 2012/0203095 | A1 * | 8/2012 | Krieger ................ G01R 33/287 606/129 |
| 2018/0000446 | A1 | 1/2018 | Lu et al. |

FOREIGN PATENT DOCUMENTS

| | | | |
|---|---|---|---|
| JP | H05-300903 A | 11/1993 | |
| JP | 2005-192915 A | 7/2005 | |
| JP | 2005-211089 A | 8/2005 | |
| JP | 2006-304923 A | 11/2006 | |
| JP | 2008-289800 A | 12/2008 | |
| KR | 10-2015-0081011 A | 7/2015 | |
| KR | 10-2018-0000523 A | 1/2018 | |
| KR | 10-2018-0027055 A | 3/2018 | |
| WO | WO-2015189843 A1 * | 12/2015 | ......... A61B 17/0401 |

OTHER PUBLICATIONS

European Communication dated Sep. 8, 2022 issued in European Patent Application No. 19909164.6.

International Written Opinion and Search Report dated Nov. 19, 2019 issued in International Patent Application No. PCT/KR2019/009072 (partial English translation).

Korean Office Action dated Oct. 16, 2023 issued in Korean Patent Application No. 10-2019-0002187 (with English translation).

European Office Action dated Apr. 18, 2024 issued European Patent Application No. 19 909 164.6.

Korean Office Action dated Jun. 18, 2024 issued in Korean Patent Application No. 10-2019-0002187 (with English translation).

\* cited by examiner

ULTRASONIC PROBE

CROSS-REFERENCE OF RELATED APPLICATIONS

This application is the U.S. National Phase under 35 U.S.C. § 371 of International Patent Application No. PCT/KR2019/009072, filed on Jul. 23, 2019, which in turn claims the benefit of Korean Application No. 10-2019-0002187, filed on Jan. 8, 2019, the entire disclosures of which applications are incorporated by reference herein.

TECHNICAL FIELD

The present disclosure relates to an ultrasonic probe that acquires an ultrasonic image to diagnose or treat an object using a needle.

BACKGROUND ART

An ultrasonic imaging apparatus may include an apparatus that irradiates an ultrasonic signal from a body surface of an object toward a target site in the body and obtains an image of a cross-section of soft tissues or blood flow in a non-invasive manner by using information of a reflected ultrasonic signal (ultrasonic echo signal).

In general, the ultrasonic imaging apparatus may include a main body, and an ultrasonic probe for transmitting an ultrasonic signal to an object to be diagnosed and receiving a signal reflected from the object.

During diagnosis by an ultrasonic imaging apparatus, a needle biopsy may be performed on a region suspected of having a tumor or the like inside an object. The needle biopsy may be performed using a needle inserted into the inside of the object to collect tissue.

However, when the needle inserted into the object deviates from the ultrasonic image by the ultrasonic probe, a normal tissue or organ of the object may be damaged.

Therefore, a user needs to perform a procedure so that the needle inserted into the object does not deviate from the ultrasonic image by the ultrasonic probe, but there may be a great difficulty for an unskilled user.

In order to reduce the above burden on the user, in general, a needle guide configured to guide the needle when the biopsy method is performed may be attached to the ultrasonic probe and used. The needle may be moved along the needle guide by the user to collect a target from the inside of the object.

In order to guide a needle using a needle guide, a needle guide corresponding to the size of the needle to be used may be selected, and the selected needle guide may be attached to the ultrasonic probe and used.

Therefore, the user may need to have a plurality of needle guides each corresponding to sizes of a plurality of needles to be used.

In addition, when a plurality of needles having different sizes are used, a plurality of needle guides having a size corresponding to each of the plurality of needles needs to be replaced and attached to the ultrasonic probe, so that there may be great discomfort to use.

DISCLOSURE

Technical Problem

The present disclosure is directed to providing an ultrasonic probe including a needle guide to guide a plurality of needles having different sizes.

The present disclosure is directed to providing an ultrasonic probe including a needle guide having a guide part provided to correspond to different sizes of a plurality of needles.

Technical Solution

An aspect of the present disclosure provides an ultrasonic probe including a case, a needle inserted into an object in the vicinity of the case, and a needle guide detachably mounted on the case to guide the needle, wherein the needle guide includes a base including a guide part configured such that the needle is inserted therein, and a support member configured to be movable along the guide part to support movement of the needle.

The base may further include a base body having one side coupled to the case, and the guide part may include a guide groove provided on the other side of the base body along a direction in which the needle is inserted.

The guide groove may be configured to have a different depth along the direction in which the needle is inserted.

The guide groove may be configured to have a different width along the direction in which the needle is inserted.

The guide part may include an inlet having one open end so that the needle is inserted into the guide part, and an outlet provided at the other end so that the needle is supported by the guide part.

The guide part may further include an inclined portion provided to be inclined between the inlet and the outlet.

The support member may be fixed to the guide part.

The support member may be configured such that a position at which the support member is fixed to the guide part varies depending on a diameter of the needle.

The support member may include a support member body seated on the base body, and a guide protrusion protruding from the support member body to be inserted into the guide part.

The guide protrusion may include an elastic material.

The guide protrusion may be forcibly fitted into the guide groove.

The needle may include a first needle and a second needle having a diameter larger than that of the first needle, and the support member may be fixed at a position adjacent to the outlet to guide the first needle and fixed at a position adjacent to the inlet to guide the second needle.

The guide protrusion may constitutes a guide pipe provided to support the needle inserted into the guide groove, together with the guide groove.

The needle may be supported to be movable between the guide protrusion and the guide groove.

The guide groove may include an insertion part through which the needle is inserted into the guide groove, and a fixing part through which the guide protrusion is fixed to the guide groove.

Advantageous Effects

Because an ultrasonic probe according to the present disclosure includes a needle guide provided to guide a plurality of needles having different sizes, there is no need to have a plurality of needle guides each corresponding to the sizes of the plurality of needles, so that simplification of needle guide management can be achieved.

Further, because the ultrasonic probe according to the present disclosure includes a needle guide provided to guide a plurality of needles having different sizes, so that ease of use can be improved.

MODE OF THE DISCLOSURE

The embodiments described in the present specification and the configurations shown in the drawings are only examples of preferred embodiments of the present disclosure, and various modifications may be made at the time of filing of the present disclosure to replace the embodiments and drawings of the present specification.

Like reference numbers or signs in the various drawings of the application represent parts or components that perform substantially the same functions.

The terms used herein are for the purpose of describing the embodiments and are not intended to restrict and/or to limit the present disclosure. For example, the singular expressions herein may include plural expressions, unless the context clearly dictates otherwise.

Also, the terms "comprises" and "has" are intended to indicate that there are features, numbers, steps, operations, elements, parts, or combinations thereof described in the specification, and do not exclude the presence or addition of one or more other features, numbers, steps, operations, elements, parts, or combinations thereof.

It will be understood that, although the terms first, second, etc. may be used herein to describe various components, these components should not be limited by these terms, and these terms are only used to distinguish one component from another.

For example, without departing the scope of the present disclosure, the first component may be referred to as a second component, and similarly, the second component may also be referred to as a first component.

The term "and/or" includes any combination of a plurality of related items or any one of a plurality of related items.

In this specification, the terms "front end," "rear end," "upper portion," "lower portion," "upper end" and "lower end" used in the following description are defined with reference to the drawings, and the shape and position of each component are not limited by these terms.

Hereinafter, an embodiment of the present disclosure will be described in detail with reference to the accompanying drawings.

Figure 1:
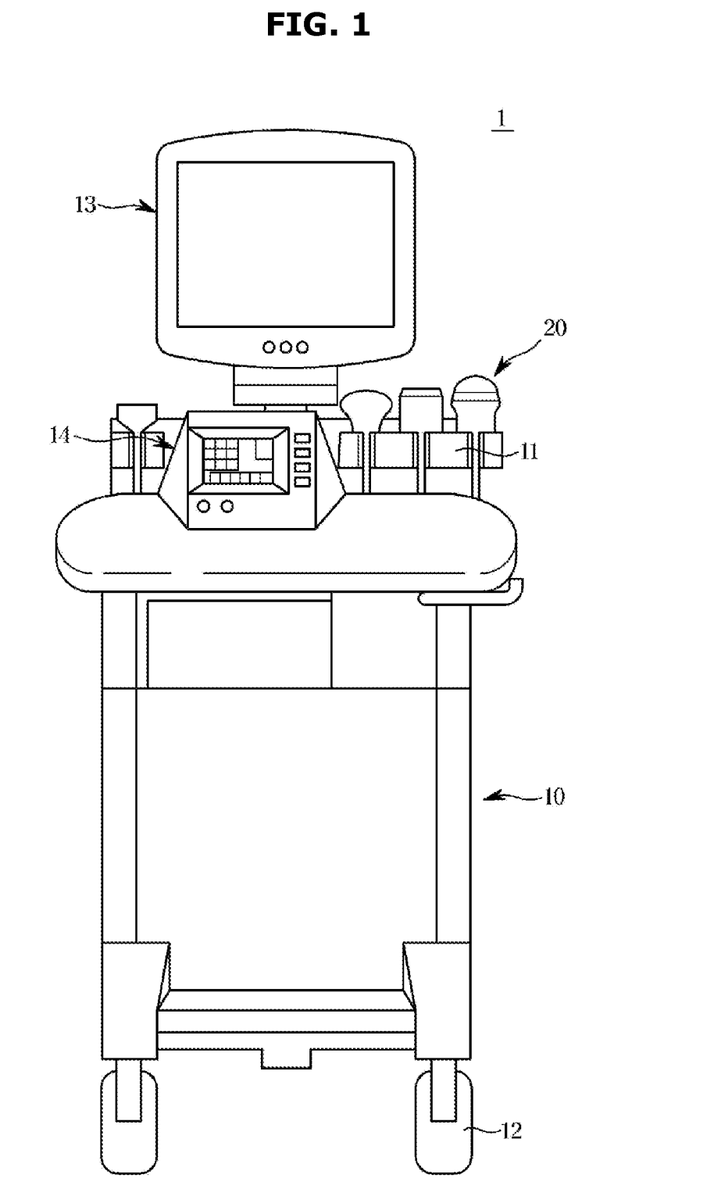
FIG. 1 is a view illustrating an ultrasonic imaging apparatus including an ultrasonic probe according to the present disclosure.

FIG. 1 is a view illustrating an ultrasonic imaging apparatus including an ultrasonic probe according to the present disclosure.

As illustrated in FIG. 1, an ultrasonic imaging apparatus 1 is a main body 10, and an ultrasonic probe 20 configured to transmit an ultrasonic signal to an object to be diagnosed and receive a signal reflected from the object.

In order to obtain an ultrasonic image of an object, the ultrasonic probe 20 may transmit an ultrasonic signal to the object and may receive an ultrasonic signal reflected from the object and transmit the reflected ultrasonic signal to a controller (not shown). The ultrasonic probe 20 may be connected to the main body 10 by a cable.

The main body 10 may be provided with a display 13 to display a diagnosis result obtained through the received ultrasonic signal. An application related to the operation of the ultrasonic imaging apparatus 1 may be displayed on the display 13.

For example, the display 13 may display an ultrasonic image obtained during an ultrasonic diagnosis process or matters related to the operation of the ultrasonic imaging apparatus 1.

The display 13 may be implemented as a cathode ray tube (CRT), a liquid crystal display (LCD), or the like. A plurality of the displays 13 may be provided. When the plurality of displays 13 is provided, the displays 13 may include a main display and a sub-display.

For example, an ultrasonic image obtained during the ultrasonic diagnosis process may be displayed on the main display, and matters related to the operation of the ultrasonic imaging apparatus 1 may be displayed on the sub-display.

The main body 10 may be provided with an input device 14. The input device 14 may be provided in the form of a keyboard, a foot switch, or a foot pedal.

When the input device 14 is a keyboard, the keyboard may be provided at an upper portion of the main body 10. When the input device 14 is a foot switch or a foot pedal, the foot switch or the foot pedal may be provided at a lower portion of the main body 10. A user may control the operation of the ultrasonic imaging apparatus 1 through the input device 14.

The ultrasonic probe 20 may be placed on the main body 10 by a holder 11. When the ultrasonic imaging apparatus 1 is not used, the user may place and store the ultrasonic probe 20 on the holder 11.

The main body 10 may be provided with a moving device 12 to move the ultrasonic imaging apparatus 1. The moving device 12 may be a plurality of casters provided on a bottom surface of the main body 10.

The plurality of casters may be aligned to allow the main body 10 to travel in a specific direction, may be arranged to allow the main body 10 to freely move, or may be locked to allow the main body 10 to stop at a specific position.

Figure 2:
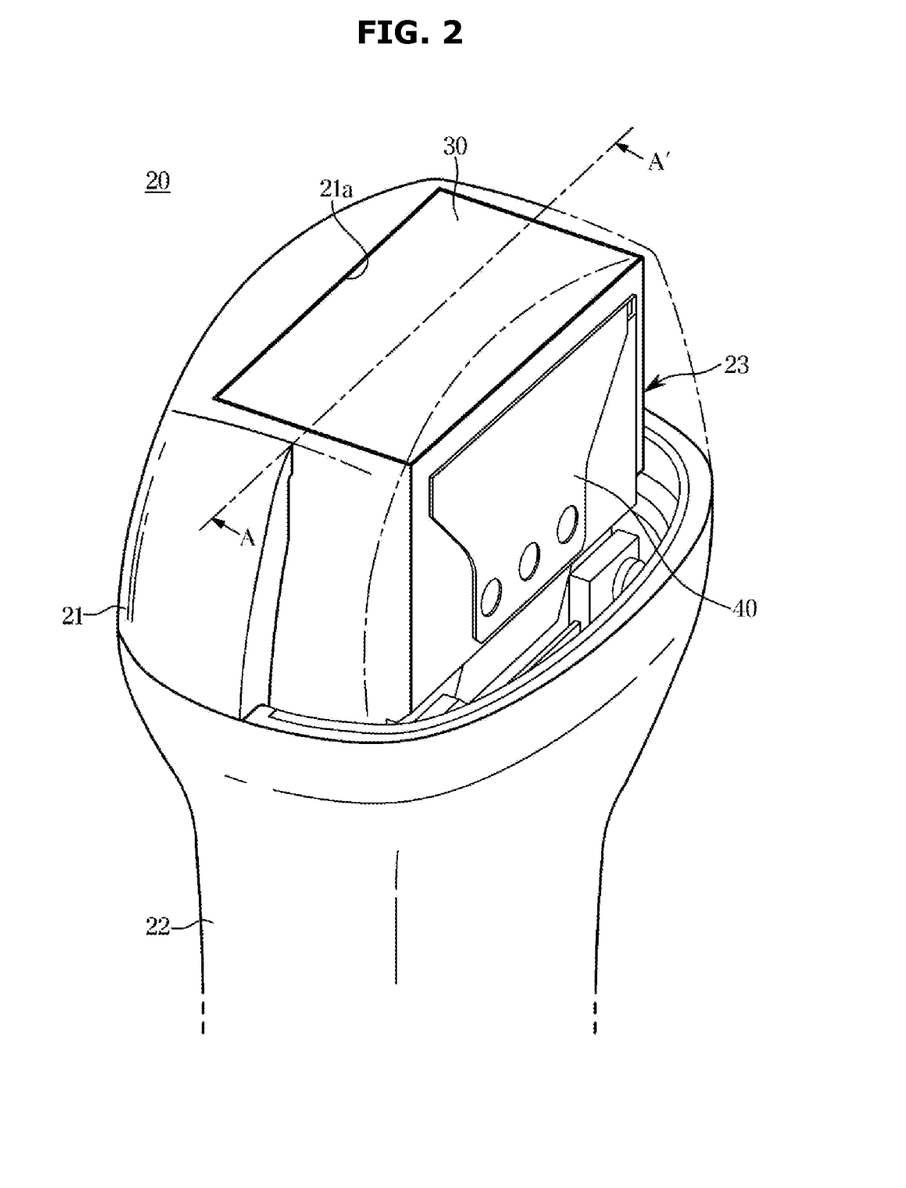
FIG. 2 is a view schematically illustrating the inside of the ultrasonic probe according to the present disclosure.
Figure 3:
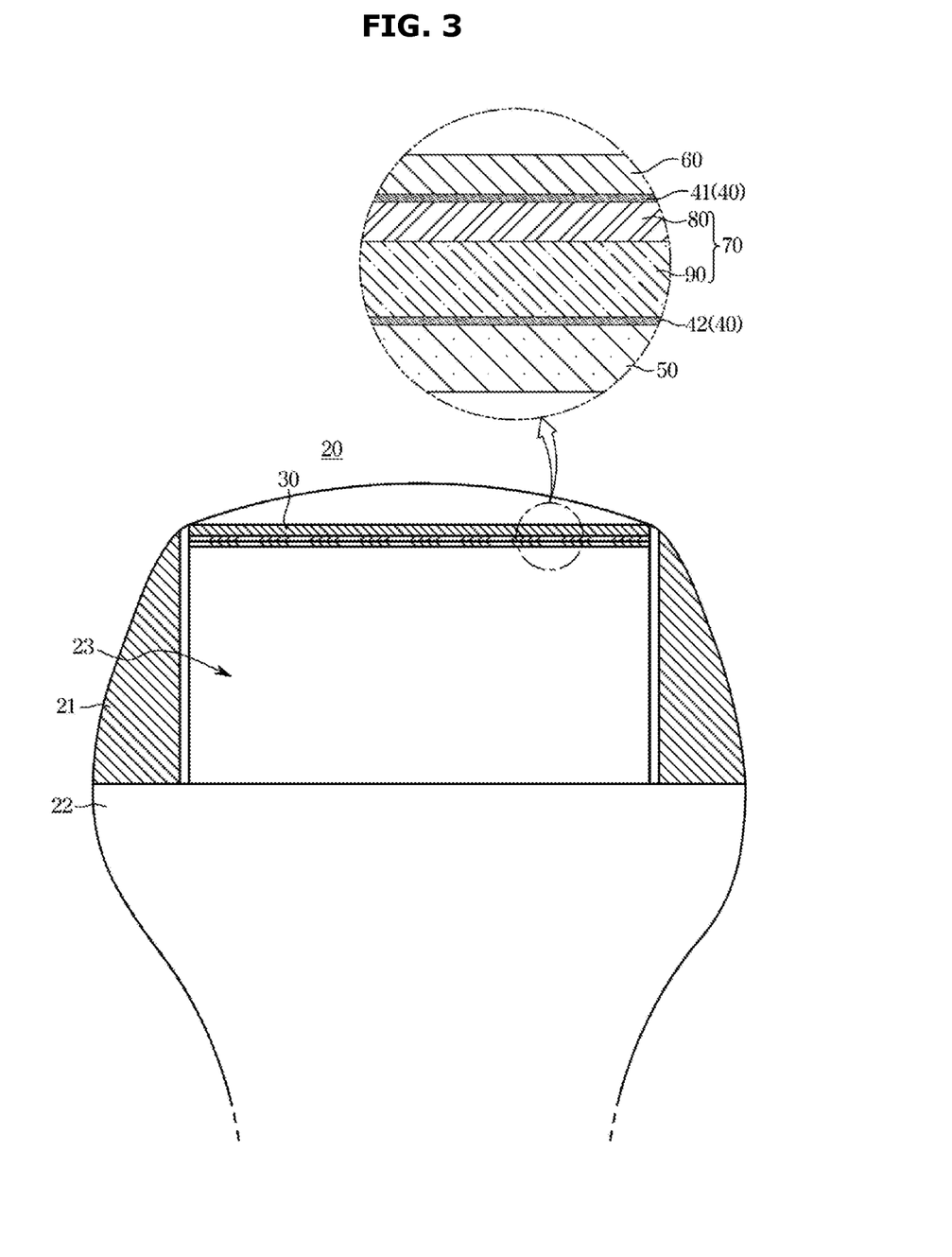
FIG. 3 is an enlarged view illustrating a part of section A-A' of the ultrasonic probe according to the present disclosure illustrated in FIG. 2.

FIG. 2 is a view schematically illustrating the inside of the ultrasonic probe according to the present disclosure. FIG. 3 is an enlarged view illustrating a part of section A-A' of the ultrasonic probe according to the present disclosure illustrated in FIG. 2.

As illustrated in FIGS. 2 and 3, the ultrasonic probe 20 according to the present disclosure may include a transducer 23 to generate an ultrasonic signal.

The ultrasonic probe 20 may include a lens 30 provided to transmit an ultrasonic signal generated from the transducer 23 to the outside. The lens 30 may focus an ultrasonic signal.

The lens 30 may be made of a material such as silicone and rubber having an acoustic impedance value similar to that of the object. The lens 30 may be provided in a convex type in which a central portion has a convex curved surface, or may be provided in a linear type having a flat surface.

The ultrasonic probe 20 may include a case 21 in which the transducer 23 is accommodated and having an opening 21a on one side such that the lens 30 is in contact with an external object, and a handle 22 mounted on the other side of the case 21.

The transducer 23 may include a transducer layer 70, a matching layer 60 disposed in the front of the transducer layer 70, and a sound-absorbing layer 50 disposed in the rear of the transducer layer 70.

In general, the transducer 23 may include a magnetostrictive ultrasonic transducer using the magnetostrictive effect of a magnetic body, a capacitive micromachined ultrasonic transducer that transmits and receives ultrasonic waves using vibrations of hundreds or thousands of finely processed thin films, or a piezoelectric ultrasonic transducer using the piezoelectric effect of a piezoelectrc material.

Hereinafter, the piezoelectric ultrasonic transducer will be described as an example of the transducer 23 according to the present disclosure.

Effects of generating a voltage when a mechanical pressure is applied to a predetermined material and causing a mechanical deformation when a voltage is applied are referred to as a piezoelectric effect and an inverse piezoelectric effect, respectively, and a material having these effects may be referred to as a piezoelectric material.

That is, the piezoelectric material may include a material that converts electrical energy into mechanical vibration energy and mechanical vibration energy into electrical energy.

The transducer layer 70 according to the present disclosure may include a piezoelectric layer 80 made of a piezoelectric material generating ultrasonic waves by converting an electrical signal into mechanical vibration, and an acoustic layer 90 disposed in the rear of the piezoelectric layer 80.

The piezoelectric layer 80, which is configured to generate ultrasonic waves using a resonance phenomenon, may be formed of a ceramic of lead zirconate titanate (PZT), a PZNT single crystal made of a solid solution of lead zinc niobate and lead titanate, a PZMT single crystal made of a solid solution of lead magnesium niobate and lead titanate, or the like.

The acoustic layer 90 may be provided to have an acoustic impedance higher than that of the piezoelectric layer 80. The acoustic layer 90 may be made of a material having electrical conductivity. A thickness of the acoustic layer 90 may be provided as ½, ¼, ⅛ or ¹⁄₁₆ of the wavelength of the piezoelectric material constituting the piezoelectric layer 80.

The acoustic layer 90 may include an acoustic reflector. The acoustic reflector may be disposed in the front of the sound-absorbing layer 50. The acoustic reflector may totally reflect ultrasonic waves traveling to the sound-absorbing layer 50. Through this configuration, a bandwidth of the ultrasonic probe 20 may be increased and the sensitivity thereof may be increased.

The acoustic reflector may be made of a material having a very high acoustic impedance to totally reflect ultrasonic waves. For example, the acoustic layer 90 may be formed of at least one of tungsten carbide and graphite composite materials.

Electrodes 40 to which an electrical signal may be applied may be formed on front and rear surfaces of the transducer layer 70, respectively. The electrodes 40 may correspond to an anode and a cathode, respectively, and may be made of a highly conductive metal such as gold, silver and copper.

A ground electrode 41 may be formed in the front of the transducer layer 70. A signal electrode 42 may be formed in the rear of the transducer layer 70. Each of the ground electrode 41 and the signal electrode 42 may be formed of a flexible printed circuit board (FPCB).

The transducer 23 may include the matching layer 60. The matching layer 60 may serve to reduce a difference in acoustic impedance between the piezoelectric layer 80 and an object so that ultrasonic waves generated from the piezoelectric layer 80 are maximally transmitted to the object.

The matching layer 60 may reduce the difference in acoustic impedance between the piezoelectric layer 80 and the object to match the acoustic impedances of the piezoelectric layer 80 and the object so that the ultrasonic waves generated in the piezoelectric layer 80 may be efficiently transmitted to the object.

The matching layer 60 may be disposed adjacent to the piezoelectric layer 80. The matching layer 60 may be located in the front of the piezoelectric layer 80. The matching layer 60 may be provided to have an intermediate value between the acoustic impedance of the piezoelectric layer 80 and the acoustic impedance of the object and may be formed of a glass or resin material.

A plurality of the matching layers 60 having different materials may be provided to be stacked such that the acoustic impedance of the matching layer 60 may gradually change from the piezoelectric layer 80 toward the object. The plurality of matching layers 60 may be formed of different materials.

The transducer 23 may include the sound-absorbing layer 50. The sound-absorbing layer 50 may be disposed adjacent to the piezoelectric layer 80. The sound-absorbing layer 50 may be located in the rear of the piezoelectric layer 80.

The sound-absorbing layer 50 can reduce pulse widths of ultrasonic waves by suppressing free vibrations of the piezoelectric layer 80 and may prevent ultrasonic images from being distorted by blocking unnecessary propagation of the ultrasonic waves to the rear of the piezoelectric layer 80.

The sound-absorbing layer 50 may be formed of a material including rubber to which an epoxy resin, tungsten powder, and the like are added.

Figure 4:
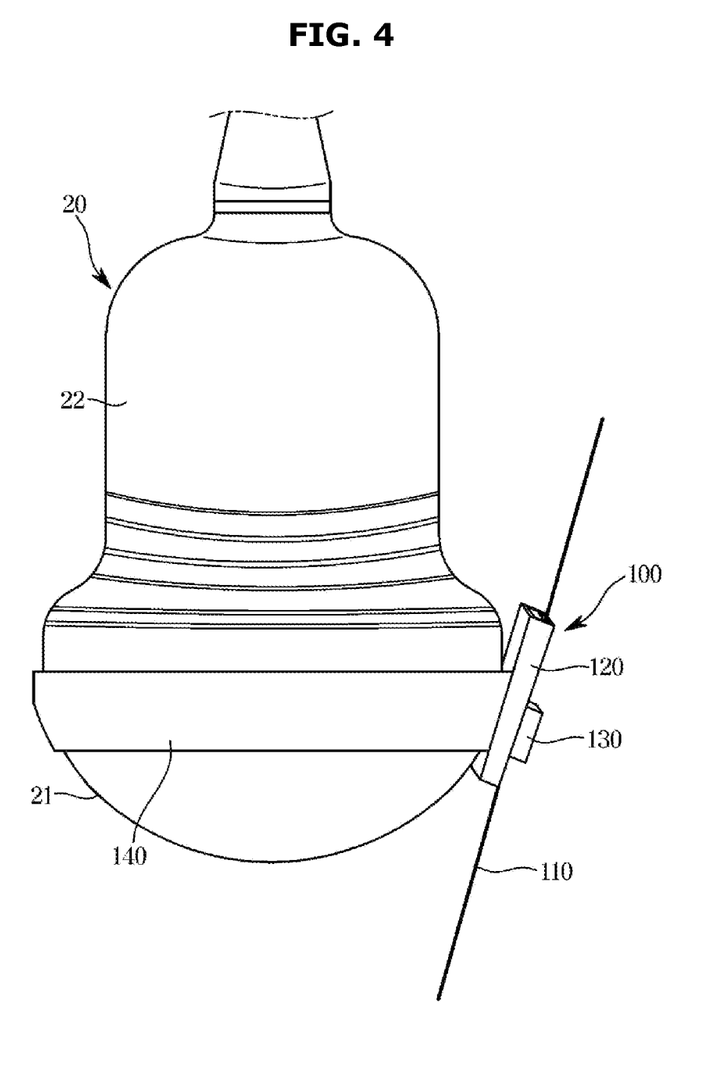
FIG. 4 is a view illustrating a needle guide coupled to the ultrasonic probe according to the present disclosure.
Figure 5:
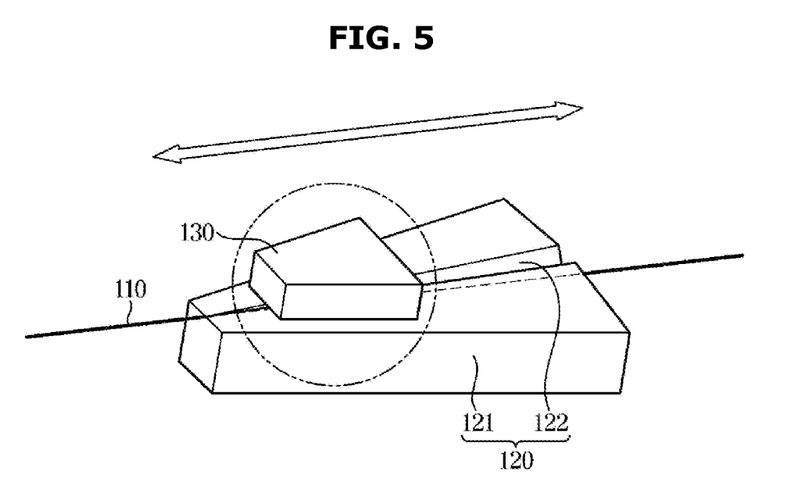
FIG. 5 is a view illustrating the needle guide separated from the ultrasonic probe according to the present disclosure.
Figure 6:
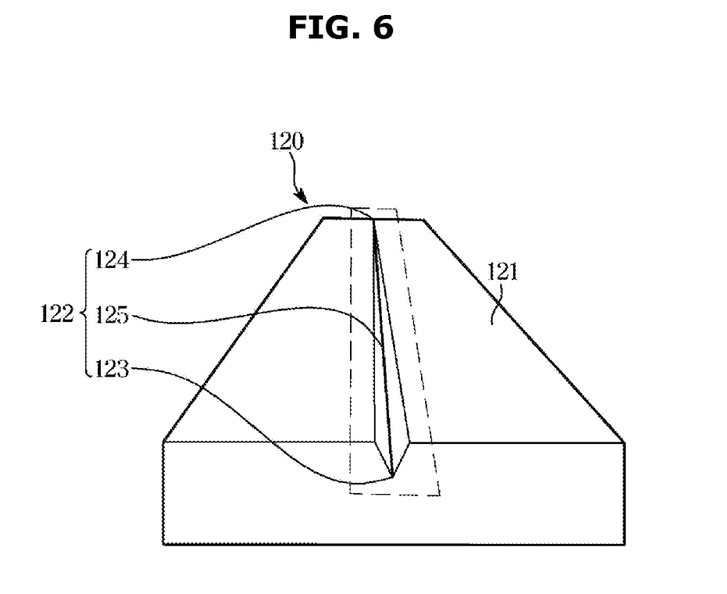
FIG. 6 is a view illustrating a guide part provided on a base in an ultrasonic probe according to the present disclosure.
Figure 7:
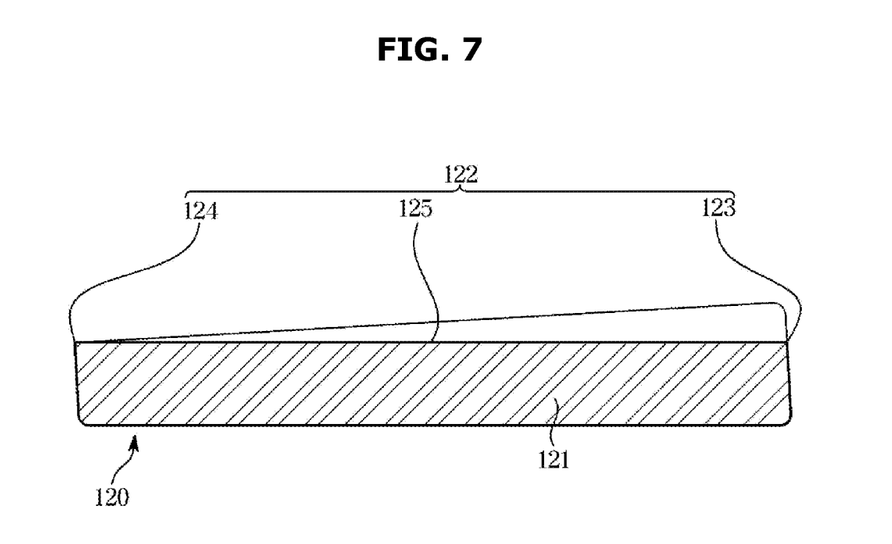
FIG. 7 is a view illustrating a cross section of the base including the guide part in the ultrasonic probe according to the present disclosure.

FIG. 4 is a view illustrating a needle guide coupled to the ultrasonic probe according to the present disclosure. FIG. 5 is a view illustrating the needle guide separated from the ultrasonic probe according to the present disclosure. FIG. 6 is a view illustrating a guide part provided on a base in an ultrasonic probe according to the present disclosure. FIG. 7 is a view illustrating a cross section of the base including the guide part in the ultrasonic probe according to the present disclosure.

As illustrated in FIGS. 4 to 7, the ultrasonic probe 20 according to the present disclosure may include a needle 110 inserted into an object in the vicinity of the case 21, and a needle guide 100 detachably mounted on the case 21 to guide the needle 110.

However, the present disclosure is not limited thereto, and the needle guide 100 may be detachably mounted to the handle 22 or may be detachably mounted to the case 21 and the handle 22.

The needle guide 100 may include a mounting member 140 provided to be detachably mounted to the case 21 or the handle 22. The mounting member 140 may include a rubber band having an elastic material. The mounting member 140 may surround the case 21 or the handle 22.

However, the present disclosure is not limited thereto, and the mounting member 140 may be configured to be flexible, such as a bracket made of plastic or the like, and may be variously provided within a limit in which the mounting member 140 may be firmly fastened to the ultrasonic probe 20 having various sizes and shapes.

The needle guide 100 may include a base 120 detachably coupled to the mounting member 140. However, the present disclosure is not limited thereto, and the base 120 may be integrally formed with the mounting member 140.

The base 120 may include a base body 121 having one side coupled to the case 21 and a guide part 122 provided such that the needle 110 is inserted. The guide part 122 may be provided on the other side of the base body 121.

The base body 121 may have a substantially trapezoidal shape. However, the present disclosure is not limited thereto.

The guide part 122 may include a guide groove 122a (see FIG. 8) provided on the other side of the base body 121 along a direction in which the needle 110 is inserted. The guide groove 122a may be depressed inward from the other side of the base body 121.

The guide groove 122a may be configured to have a different depth along the direction in which the needle 110 is inserted. The guide groove 122a may be configured to have a different width along the direction in which the needle 110 is inserted.

The depth of the guide groove 122a may decrease along the direction in which the needle 110 is inserted, and the width of the guide groove 122a may decrease along the direction in which the needle 110 is inserted.

A cross section of the guide part 122 may include a triangular shape. The guide part 122 may include a slope. However, the present disclosure is not limited thereto.

The guide part 122 may include an inlet 123 provided at one end thereof such that the needle 110 is inserted into the guide part 122, and an outlet 124 provided at the other end thereof such that the needle 110 is supported by the guide part 122.

One side of the inlet 123 may be open such that the needle 110 is inserted into the guide part 122, and one side of the outlet 124 may be closed such that the needle 110 is supported by the guide part 122.

The guide part 122 may include an inclined portion 125 provided to be inclined between the inlet 123 and the outlet 124. The inclined portion 125 may be inclined downward from the inlet 123 toward the outlet 124. However, the present disclosure is not limited thereto.

The needle 110 may enter the inlet 123, move while being guided along the inclined portion 125, and protrude to the outside of the guide part 122 through the outlet 124.

A plurality of the needles 110 having different diameters may be provided. The needle 110 may include a first needle 111 (see FIG. 8) and a second needle 112 (see FIG. 9) having a diameter larger than that of the first needle 111.

As the needle guide 100 according to the present disclosure includes a guide part 122 configured to have a slope and vary in depth and width along the direction in which the needle 110 is inserted, the needle guide 100 may guide the plurality of needles 110 having different diameters including the first needle 111 or the second needle 112.

That is, without the need to use a plurality of the needle guides 100 corresponding to respective diameters of the plurality of needles 110, only one of the needle guide 100 may guide all of the plurality of needles 110 having different diameters.

The needle guide 100 may include a support member 130 provided to support movement of the needle 110. The support member 130 may be configured to be movable along the guide part 122.

The support member 130 may move along the guide part 122 in the same direction as the movement direction of the needle 110 that is inserted into the guide part 122.

That is, the needle guide 100 according to the present disclosure may guide the needle 110 with one of the guide part 122 and movably fix the support member 130. Therefore, a separate fixing structure for fixing the support member 130 may be omitted.

The support member 130 may be seated on the upper side of the base 120. The support member 130 may be detachably coupled to the upper side of the guide part 122.

A size of the support member 130 may be smaller than a size of the base 120. However, the present disclosure is not limited thereto.

The support member 130 may be detachably fixed to the base 120. The support member 130 may be fixed to the guide part 122. The support member 130 may be forcibly fitted into the guide part 122. The support member 130 may include an elastic material.

As support member 130 includes an elastic material, the support member 130 may be fixed to the inlet 123 having a relatively high height and a wide width, and may also be fixed in the vicinity of the outlet 124 having a relatively low height and a narrow width.

That is, the support member 130 may be fixed at an arbitrary position of the guide part 122 along the inclined portion 125 from the inlet 123 to the outlet 124.

The support member 130 may include a support member body 131 seated on the base body 121, and a guide protrusion 132 protruding from the support member body 131 to be inserted into the guide part 122.

The support member body 131 may have a substantially trapezoidal shape. However, the present disclosure is not limited thereto.

The guide protrusion 132 may protrude downward from the support member body 131. The guide protrusion 132 may protrude from the support member body 131 toward the guide part 122.

The guide protrusion 132 may be detachably fixed to the guide part 122. The guide protrusion 132 may be forcibly fitted into the guide groove 122a. The guide protrusion 132 may include an elastic material.

That is, the support member body 131 may be made of a material that does not have elasticity, and the guide protrusion 132 may be made of a material having elasticity.

The guide protrusion 132 may be detachably coupled from the support member body 131. However, the present disclosure is not limited thereto, and the guide protrusion 132 may be formed integrally with the support member body 131.

The needle 110 may be movably supported between the guide protrusion 132 and the guide groove 122a. The needle 110 may be movably guided between the base 120 and the support member 130 fixed to the base 120 by the guide protrusion 132 and the guide part 122.

As the ultrasonic probe 20 according to the present disclosure includes the base 120 including the guide part 122 and the support member 130 including the guide protrusion 132, and the guide protrusion 132 is movably fixed along the guide part 122, the ultrasonic probe 20 may guide the plurality of needles 110 having different diameters including the first needle 111 or the second needle 112.

Figure 8:
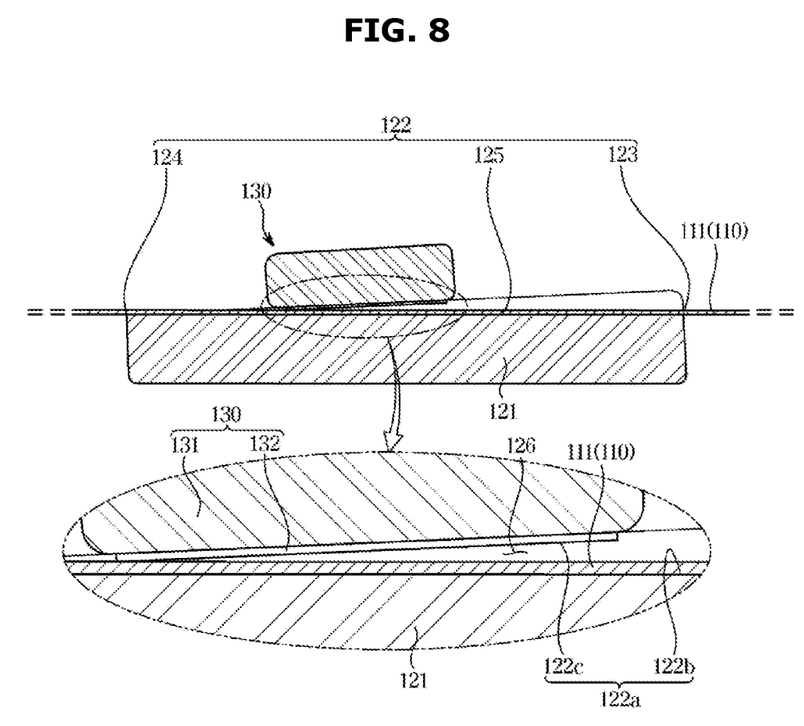
FIG. 8 is a view illustrating a state in which a first needle is supported on the needle guide in the ultrasonic probe according to the present disclosure.
Figure 9:
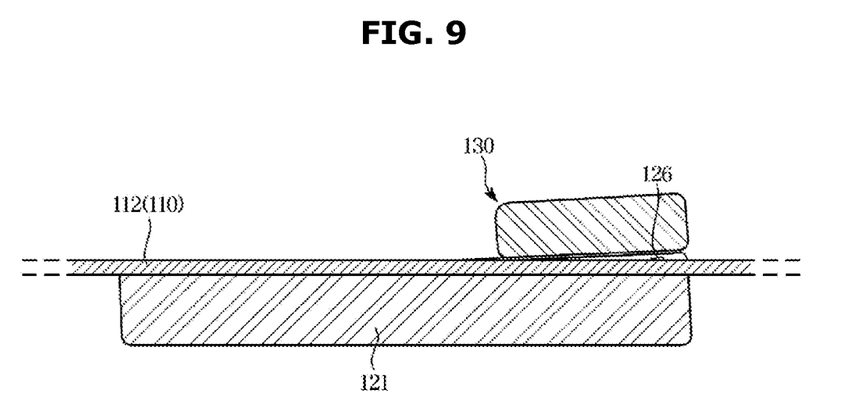
FIG. 9 is a view illustrating a state in which a second needle is supported on the needle guide in the ultrasonic probe according to the present disclosure.

FIG. 8 is a view illustrating a state in which a first needle is supported on the needle guide in the ultrasonic probe according to the present disclosure. FIG. 9 is a view illustrating a state in which a second needle is supported on the needle guide in the ultrasonic probe according to the present disclosure.

Hereinafter, a structure in which the needle guide 100 according to the present disclosure guides the plurality of needles 110 having different diameters will be described in detail.

As illustrated in FIGS. 8 and 9, the support member 130 according to the present disclosure may be configured such that a position at which the support member 130 is fixed to the guide part 122 varies depending on the diameter of the needle 110. The needle 110 may include the first needle 111 and the second needle 112 having a diameter larger than that of the first needle 111.

The support member 130 may be fixed at a position adjacent to the outlet 124 to guide the first needle 111. The support member 130 may be fixed at a position adjacent to the inlet 123 to guide the second needle 112.

That is, when the needle 110 is not inserted into the guide part 122, the guide protrusion 132 of the support member 130 may be fitted and fixed to the guide part 122 at a position closest to the outlet 124 of the guide part 122. The size of the guide protrusion 132 may be larger than the size of the guide groove 122a.

However, when the needle 110 is inserted into the guide part 122, the position at which the guide protrusion 132 is fitted and fixed to the guide part 122 may vary depending on the diameter of the needle 110.

Because the guide part 122 is configured to decrease in depth and width from the inlet 123 toward the outlet 124, the diameter of the second needle 112, which is any one of the plurality of needles 110, may be larger than the depth or width of an arbitrary position of the guide part 122.

The guide protrusion 132 may be fitted and fixed to the guide part 122 to be spaced apart from the needle 110 such that the needle 110 is inserted into the guide part 122 and the needle 110 inserted in the guide part 122 is movable.

The guide part 122 may constitute a guide pipe 126, which is provided to have a different size depending on the diameter of any one of the plurality of needles 110 inserted into the guide part 122, together with the support member 130.

The guide pipe 126 may include a space between the guide part 122 and the guide protrusion 132 fitted to the guide part 122. The guide pipe 126 may include a space between the guide protrusion 132 and the inclined portion 125 of the guide part 122.

The guide pipe 126 may be larger than the diameter of the needle 110 so that the needle 110 may be moved inside the guide pipe 126. The guide part 122 may include an insertion part 122b through which the needle 110 is inserted into the guide part 122, and a fixing part 122c through which the guide protrusion 132 is fixed to the guide part 122.

The guide groove 122a may include the insertion part 122b into which the needle 110 is inserted into the guide groove 122a, and the fixing part 122c on which the guide protrusion 132 is fixed to the guide groove 122a.

The guide pipe 126 may be larger than the insertion part 122b. The guide pipe 126 may include the insertion part 122b and a space in which the needle 110 inserted into the guide part 122 and the guide protrusion 132 are spaced apart. The guide part 122 may include the guide pipe 126 and the fixing part 122c.

A size of the inlet 123 may be larger than the diameter of the needle 110 inserted into the guide part 122. Therefore, the needle guide 100 according to the present disclosure may guide the plurality of needles 110 having a diameter less than or equal to the size of the inlet 123.

While the present disclosure has been particularly described with reference to a specific embodiment, but the scope of rights of the present disclosure is not limited to these embodiments.

Various embodiments that may be modified or modified by those skilled in the art of the present disclosure would also be within the scope of the present disclosure, without departing from the gist of the present disclosure specified in the claims.

The invention claimed is:

1. An ultrasonic probe comprising:
a case;
a needle inserted into an object in the vicinity of the case; and
a needle guide detachably mounted on the case to guide the needle,
wherein the needle guide comprises:
a base comprising a guide part configured such that the needle is inserted therein; and
a support member configured to be movable along the guide part to support movement of the needle,
wherein the guide part comprises a guide groove provided on the base along a first direction in which the needle is inserted and configured to have a different depth along the first direction so that a plurality of needles having different diameters are insertable in the guide groove,
wherein the support member is configured to be movable along the guide groove in the first direction, and configured such that a position of the support member on the guide groove varies along the first direction depending on a diameter of the needle,
wherein the support member comprises a support member body seated on the base and a guide protrusion protruding from the support member body to be inserted into the guide groove,
wherein the guide protrusion comprises an elastic material,
wherein the guide part further comprises:
an inlet having one open end so that the needle is inserted into the guide part;
an outlet provided at the other end so that the needle is supported by the guide part; and
an inclined portion provided to be inclined between the inlet and the outlet,
wherein a cross section of an inlet of the guide part is a triangular shape such that the needle is guided to the inclined portion to prevent the needle from getting out from the guide part,
wherein the guide groove is configured to have a different width along the first direction in which the needle is inserted, and
wherein an inner surface of the guide protrusion is inclined with a bottom surface of the guide groove in the first direction.

2. The ultrasonic probe according to claim 1, wherein the base further comprises a base body having one side coupled to the case, and the guide groove is provided on the other side of the base body along the first direction in which the needle is inserted.

3. The ultrasonic probe according to claim 2, wherein the support member body is seated on the base body.

4. The ultrasonic probe according to claim 3, wherein the guide protrusion is forcibly fitted into the guide groove.

5. The ultrasonic probe according to claim 1, wherein the needle comprises a first needle and a second needle having a diameter larger than that of the first needle, and the support member is fixed at a position adjacent to the outlet to guide the first needle and fixed at a position adjacent to the inlet to guide the second needle.

6. The ultrasonic probe according to claim 3, wherein the guide protrusion constitutes a guide pipe provided to support the needle inserted into the guide groove, together with the guide groove.

7. The ultrasonic probe according to claim 6, wherein the needle is supported to be movable between the guide protrusion and the guide groove.

8. The ultrasonic probe according to claim 3, wherein the guide groove comprises: an insertion part through which the needle is inserted into the guide groove; and a fixing part through which the guide protrusion is fixed to the guide groove.

\* \* \* \* \*